(12) United States Patent
Breslavets et al.

(10) Patent No.: US 11,574,405 B2
(45) Date of Patent: Feb. 7, 2023

(54) ANALYSIS OF THE SEVERITY OF SKIN DISEASE THROUGH ENTROPY QUANTIFICATION

(71) Applicant: Dr. Maksym Breslavets Medicine Professional Corp., Whitby (CA)

(72) Inventors: Maksym Breslavets, Toronto (CA); Alina Breslavets, Toronto (CA)

(73) Assignee: Dr. Maksym Breslavets Medicine Professional Corp., Whitby (CA)

(*) Notice: Subject to any disclaimer, the term of this patent is extended or adjusted under 35 U.S.C. 154(b) by 165 days.

(21) Appl. No.: 16/773,633

(22) Filed: Jan. 27, 2020

(65) Prior Publication Data

US 2020/0250825 A1    Aug. 6, 2020

Related U.S. Application Data

(60) Provisional application No. 62/799,227, filed on Jan. 31, 2019.

(51) Int. Cl.
*G06T 7/00* (2017.01)
*A61B 5/00* (2006.01)

(52) U.S. Cl.
CPC .......... *G06T 7/0014* (2013.01); *A61B 5/445* (2013.01); *A61B 5/4842* (2013.01); *G06T 2207/30088* (2013.01)

(58) Field of Classification Search
CPC ........... G06T 7/0012; G06T 7/0014; G06T 2207/30088; A61B 5/445; A61B 5/4842; A61B 2576/00
See application file for complete search history.

(56) References Cited

U.S. PATENT DOCUMENTS

| | | | |
|---|---|---|---|
| 8,649,589 B2 | 2/2014 | Gareau | |
| 10,078,897 B2 | 9/2018 | Shupp | |
| 2009/0080727 A1* | 3/2009 | Cotton | G06T 7/42 382/128 |
| 2011/0064287 A1* | 3/2011 | Bogdan | G06T 7/42 382/128 |
| 2011/0286643 A1* | 11/2011 | Kislal | G06T 7/0012 382/128 |
| 2016/0100789 A1* | 4/2016 | Huang | A61B 5/7246 600/306 |
| 2017/0224270 A1* | 8/2017 | Stamnes | G06K 9/4661 |
| 2017/0241985 A1 | 8/2017 | Lachman | |
| 2020/0170564 A1* | 6/2020 | Jiang | G06K 9/4628 |

FOREIGN PATENT DOCUMENTS

JP         2009082338 A  *  4/2009

* cited by examiner

*Primary Examiner* — Brenda C Bernardi
(74) *Attorney, Agent, or Firm* — Cherskov Flanynik & Gurda, LLC

(57) ABSTRACT

The present invention provides an analysis and method of quantifying the severity of skin diseases through the skin exhibited entropy. Quantitative analysis and evaluation of skin is a new, non-invasive, quick, and reproducible method of assessing skin disease and skin disease progression. The quantitative analysis of the skin disease applies a entropy algorithm to quantify the severity of the disease and compared to healthy skin. The method is applied in determination of the severity of the skin disease or applied to determine the effectiveness of the subsequent treatment modalities. It is highly reproducible and removes physician's own bias and past experience.

5 Claims, 6 Drawing Sheets
(5 of 6 Drawing Sheet(s) Filed in Color)

ANALYSIS OF THE SEVERITY OF SKIN DISEASE THROUGH ENTROPY QUANTIFICATION

PRIORITY CLAIM

This utility application claims priority to U.S. Provisional Application 62/799,227, titled "Analysis of the Severity of the Skin Disease Through Entropy Quantification" filed on Jan. 31, 2019, the contents of which are hereby incorporated by reference.

FIELD OF THE INVENTION

This invention relates to the assessment of the severity of skin disease through quantitative analysis of topical skin imaging. The system and method disclosed herein are directed to non-invasive clinical imaging, and, more particularly, to non-invasive imaging of the skin to assess and determine topological entropy.

BACKGROUND

Skin damage is a universal problem that affects every individual. Skin, being the largest human organ, and the first defensive barrier to the external environmental factors, is exposed to and is continuously damaged. The skin, acts as a barrier against all forms of environmental stress, including but not limited to: uv-radiation; oxidization; free radicals; particulates; tropospheric ozone; and, anti-microbials. Other external factors that affect the skin includes high and/or low temperatures; high and/or low humidity; and air pressure. The skin is also affected by a large number of internal factors. Many auto-immune and auto-inflammatory diseases directly affect the skin and damage it for within. As a defensive barrier, the skin is often damaged by the internal and external factors. All of the factors described above could be an element to cause the skin to become damaged, or skin diseased.

The damage of the skin can be expressed through various skin expression profiles. The profiles are generally similar, as skin damage occurs through a specific and regulated mechanism. These profiles translate into reddening of the skin through inflammation, scaling, dryness, and formation of lesions.

Each skin condition has its own disease progression. The progression of the skin disease is often difficult to assess. Beyond the generalities of visualization of lesions and open wounds, skin damage is often hard to characterize and quantify.

Quantitative analysis is even harder to determine. In general, physicians assess skin disease based on subjective visual inspection. The physicians are usually biased by their experiences, the types of skin diseases they encounter regularly, and by their education.

Psoriasis, a common skin disease has been used as reference disease to analyze and discuss current measuring tools as well as propose a new approach for skin measurement.

One of the traditional methods for assessment psoriasis, is through Psoriasis Area and Severity Index (PASI). PASI measures the average value for the redness, thickness and scaliness of presented lesion on a scale of 0-4 taking into account the involvement of body surface area (BSA). PASI provides a clinical value from 0 to 72. Despite its wide usage and definition of all key elements, the PASI is time consuming and falls short in its inability to reflect on clinical use and consistency.

In addition to PASI, Physician Global Assessment (PGA) is also an accepted method of quantification of skin diseases. PGA helps dermatologists develop an objective and standardized measure that can be used in the clinical setting. The following clinical variables are assessed for the PGA—psoriatic plaque induration, erythema, and scaling. Each value has been given a word-based terminology and description. PGA fails in that each value is hard to interpret and there is no consensus on each value. Additionally, the PGA fails to provide consistent and reproducible result.

Various attempts have been made to standardize skin assessment. The standardization includes the analysis of a skin image through various mechanisms. Prior publications such as U.S. Pat. No. 8,649,589 (Gareau), U.S. Pat. No. 10,078,897 (Shupp) and, U.S. Patent Application No.: 2017/0241985 (Lachman) provide such examples of a non-invasive method and system of characterizing skin in a quantitative manner.

Gareau discloses a method of non-invasive assessment of a skin element called keratinocytes. The pattern and arrangement of the keratinocytes on the skin is a determinative of the formation of skin cancer. Gareau uses non-invasive confocal imaging to capture the skin surface. The resultant digital image is processed to identify cells and an automated algorithm determines the location of the keratinocytes. Gareau assesses the skin in the algorithm through pattern formation. The distribution of keratinocytes is grid-like, with a regular spatial frequency. The absence of the normal pattern of keratinocytes has a specificity of 87.5% and 52.1% respectively for melanoma detection. The pattern of keratinocytes is even more important in distinguishing between actinic keratoses and normal skin. Gareau attempt to reduce the frequency of invasive biopsies required to detect cancer through the use of non-invasive imaging with cellular resolution which include: confocal microscopy, high frequency ultrasound, optical coherence tomography, and, photo- thermal microscopy. Gareau analyses a number of images of the skin, which are considered to be healthy and potentially cancerous, and using an algorithm of:

$$R = \mathrm{erf}\left(\frac{x-a}{b}\right) \text{ and substituting } r = sqrt(x^2 + y^2) \text{ for } X$$

The limitation with Gareau relates what is assessed within the digital images. The method analyses the location and arrangement of keratinocytes. In doing so, and with the aid of the algorithm, the method can accurately determine malignancy. The problem with Gareau is that it is unable to provide additional insight on the general condition of the skin in relation to other diseases. It also fails to determine the general entropy of the skin. Furthermore, the method fails as it does not provide additional guidance on the quantitative assessment of the skin disease as it does not provide a numerical value for the arrangement of keratinocytes.

Shupp discloses a method for burn wound assessment, and more particularly, to the system and methods that can identify areas of burn wound conversion using an imaging modality. The assessment identifies burn wound conversion through non-contact imaging. The imaging, which is performed over a period of time, can accurately determine the burn would undergoing conversion at much earlier time point than with current techniques. The assessment is accomplished automatically by a system comprising a processor. As background, burn wounds are assesed under the Jackson model. The model provides concentric zones related to the burn wound: the zone of necrosis, the zone of stasis, and the zone of hyperemia. The tissue within the zone of stasis is potentially viable, but risks undergoing burn wound conversion. The method in Shupp determines areas of the burn wound that are undergoing conversion at an early stage, thereby providing the physicians the ability to correctly assess the burn wound and formulate the correct medical procedure. Images that are analyzed by the Shupp method are obtained by Active dynamic thermography (ADT) and Laser Doppler Imaging. The burn wound is stimulated by stimulation lamps that are positioned four inches above the surface of the burn and angled to face the center and applied for 6000 ms. The reaction of the burn wound to the stimulation is recorded and the video imaging is analyzed via thermal flux, as it is a change in temperature as a function of time, and calculated:

$$\text{Thermal Flux}\left(\frac{\delta T}{\delta t}\right) = \sum_{0}^{150 \text{ frames}} \frac{\Delta^\circ \text{C.}}{\frac{1}{30} \text{ second}}$$

As with Gareau, the Shupp method falls short in that it is specific to the indication, namely, burn wounds. Shupp cannot assess all skin indications as it focuses only on assessing the burn wound markers. Furthermore, the method as described in Shupp does not provide for a quantitative analysis. Although, the method in Shupp does assess the burn wound using gradient analysis, that analysis applies to the gradual change of the burn wound as a result of the stimulation. The method does not allow for the quantitative assessment of the burn wound which would provide for an accurate determination of the burn wound along the progression at the time the images were captured. Finally, the imaging tools required are expensive and, although are considered non-invasive, are very obtrusive.

Lachman discloses a method of determining the relief of the skin surface of a subject that is subsequently translated into the degree of maturation of the skin. Through the analysis of the skin topology, Lachman determines the skins critical features including but not limited to: organization; mechanical properties; and, sensorial features. The method provides a reliable and reproducible results that quantitatively the maturation of the skin topography in children. Through comparison of skin at various ages and from infants to adults provides the Lachman method a reproducible and quantitative timeline as the baseline and the development of the skin at various time points. The baseline is applied to subsequent skin imaging to determine the skin maturation. Skin is a highly non-linear, anisotropic, viscoelastic and nearly incompressible material. Its properties vary with age, from site to site and per person. This leads to difficulties in obtaining quantitative description of mechanical properties of the skin. Lachman method assesses the relief, and the degree of maturation of the skin through assessment of the skin in children. To calculate the developed skin surface of a sample, Lachman applies the root mean square plane method. This method aims at minimizing the variations in relation to each of the coefficients of the average plant.

Furthermore, and according to another aspect of the Lachman patent, the level of maturation of the skin can be used to characterize skin disorders affecting children. Skin disorders result in injuries, which correspond to damaged skin or a skin in prod condition. This has deleterious effect on the skin's organizational, mechanical, and sensorial properties, including its capacity to resist to aggression. Such effects could translate into an alteration of the maturation level of the skin. A quantitative method of cutaneous relief imaging is applied by Lachman, wherein the topographical profile is considered as a distribution of heights spaced out at regular intervals. The method thus makes use of quantitative parameters which enable monitoring the changes of the skin surface relief. In addition, both micro- and macro-reliefs can be analyzed. The method enables the determination of the developed skin surface which corresponds to the ratio between the area of the local surfaces and measured zones. The developed surface is calculated using:

$$S_{Dev} = \frac{\sum_{j=1}^{N-1}\sum_{i=1}^{M-1} A_{ij}}{\text{Length} \times \text{Width}}$$

The algorithm provides a numerical value that can then be implemented in determining the maturation of the skin. Lachman fails in assessing the entropy of the skin and the various alterations that are a direct result of inflammatory, neoplastic or traumatic alterations. It fails at providing the determination of the progression of the skin disease.

As such, there is a need for a quantitative assessment of the skin that is reproducible and accurate with all skin diseases. A method that allows for fast and effective determination of the progression of the various skin diseases which, in turn, will provide the physicians with a better tool to provide effective treatment. The need also requires the method to use imaging tools that are readily available which can also develop the resultant images for analysis quickly.

SUMMARY

The present invention provides an analysis and method of quantifying the severity of skin diseases through the skin exhibited entropy. Quantitative analysis and evaluation of skin is a new, non-invasive, quick, and reproducible method of assessing skin disease and skin disease progression. The analysis and method described herein can be applied to various skin assessments in the medical industry. The method can be applied to determine the severity of the skin disease or can be applied to the effectiveness of the subsequent treatment modalities. It is highly reproducible and removes physician's own bias and past experience.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

It will now be convenient to describe the invention with particular reference to one embodiment of the present invention. It will be appreciated that the drawings relate to one embodiment of the present invention only and are not to be taken as limiting the invention.

DETAILED DESCRIPTION

Figure 1:
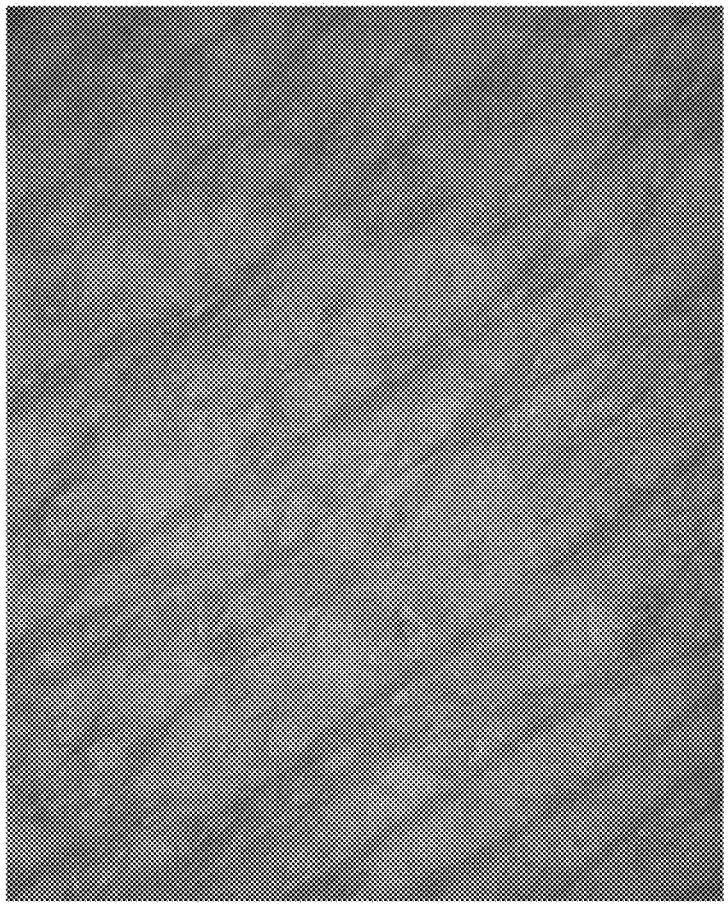
FIG. 1 is a representative image of healthy skin, according to one embodiment of the present invention.

The present invention will now be described more fully hereinafter with reference to the accompanying images, in which preferred and other embodiments of the invention are shown. No embodiment described below limits any claimed invention and any claimed invention may cover processes or element that are not described below. The claimed inventions are not limited to products or elements having all the features of any one element or process described below or to features common to multiple or all of the elements described below. It is possible that an element or process described below is not an embodiment of any claimed invention. The applicants, inventors or owners reserve all rights that they may have in any invention claimed in this document, for example the right to claim such an invention in a continuing application and do not intend to abandon, disclaim or dedicate to the public any such invention by its disclosure in this document.

References are made to the accompanying drawings which form a part hereof, and in which are shown by way of illustration embodiments that may be practiced. It is to be understood that other embodiments may be utilized, and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The description may use the terms "embodiment" or "embodiments", which may each refer to one or more of the same or different embodiments. Furthermore, the terms "comprising", "including", "having", and the like, as used with respect to embodiments, are synonymous, and are generally intended as open terms (the term "including" should be interpreted as "including but not limited to", the term "having" should be interpreted as "having at least", the term "includes" should be interpreted as "includes but is not limited to").

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Quantitative analysis of skin diseases is a key element to not only detection of certain diseases, but also in the subsequent assessment of the disease progression. Detection of skin diseases normally starts with the visualization of the skin, and its cell composition. A physician assesses the size, shape, and distribution of various skin elements to determine the type of skin disease and the state of the disease. A pathologist might assess the biopsy of the skin disease to determine the disease and the progression. This is quite invasive and time consuming.

Embodiments described herein provide methods for non-invasive quantitative assessment of the skin diseases. The assessment of a skin disease is accomplished through the use of a processor that applies a computer algorithm to the digital image of a skin disease to determine the level of entropy of the skin. This level is then compared to the level of entropy of an image of a non-diseased (or healthy) skin of the same patient. Furthermore, the processor analyzes the entropy of the diseased skin in relation to the healthy skin and provides a quantitative analysis that is reproducible. The skin disease is not limited, as the quantitative assessment can be utilized for almost all skin diseases. In the current embodiment of the present invention, psoriasis was assessed by the method and the analysis. A worker skilled in the relevant art would appreciate the various skin conditions that could be assessed.

In accordance with the embodiment, the method compares, by one or more computing devices, an image segment of the skin disease to a known healthy skin images segment to determine the degree of entropy within the diseased skin segment image. The degree of entropy is given a value by the method and corresponding calculation with the provided algorithm.

Calculation of Entropy

The method of this invention enables the quantitative assessment and characterization of the diseased skin. The diseased skin is compared to healthy skin. Healthy skin is obtained from the individual, as it is common that an individual inflicted with a skin disease will also have skin that is physiologically and phenotypically healthy. In doing so, the variables with the skin are constant within the diseased skin and healthy skin. The variables include but are not limited to: age; general everyday stress of the skin; skin pigmentation; previous skin conditions; and, the effects of the environment on the skin. A control group of healthy skin maybe be used, but its use may affect the quantitative analysis based on the variables.

Skin

Skin is a highly non-linear, anisotropic, viscoelastic and nearly incompressible material. Its properties vary with age, from site to site and per person. This leads to difficulties in obtaining quantitative assessment of the skin's entropy. Observations of the skin made with the human eye can create more chances of making diagnostic and quantitative errors.

Skin Diseases

The quantitative method approach described herein can be applied to any skin disease or condition. The algorithm remains the same. The entropy of the skin, as a result of the skin disease is calculated using the algorithm and a quantitative score is provided based on the comparison with healthy skin. The invention herein describes the quantitative approach on Psoriasis, as the skin disease. A worker skilled in the relevant art would appreciate that the method can be applied to all skin diseases.

Skin diseases, as it is referred to herein, relates to all abnormal reactions that can affect the skin. These conditions affect all aspects of the skin, including but not limited to: the epidermis; the dermo-epidermal junction; the hypodermis; the pores; sweat glands; sebaceous glands; hair; and, the nails. Skin disorders that can be assessed by the method in the present invention relate to damage to the skin. The skin diseases encompassed within the invention include: dry skin; sun damaged skin; cold damaged, or frostbitten; stressed or pollution; irritated by pollen; eczema and other forms of dermatitis; irritant dermatitis; psoriasis; disease-Lainer Moussous, burns; open cut wounds; herpes; angiomas; hemangiomas; and, acne. Skin diseases can also encompass other types of skin disorders including but not limited to: wars; scabies; and, fungal infections.

The key element to the skin diseases is that it has manifest in a phenotypical and visual expression on the skin. The expression is calculated as the entropy.

Quantitative Assessment of Skin Diseases

The invention herein is based upon the premise that healthy skin has less entropy, and more structured, than diseased skin. Diseased skin exhibits an increased alteration, or higher level of entropy, based on a number of factors, including but not limited to: inflammation, neoplastic or traumatic processes; and physical damage associated with lacerations or burns.

A quantitative method of skin disease imaging has been developed, wherein the skin profile is determined through the expressed entropy. Healthy skin is very structured and ordered. Healthy skin displays a certain repetitive pattern. Skin creases are very structured and repetitive. Hair follicles are also very structured and form a honeycomb type pattern. Skin that is afflicted with a skin disease loses the structure and repetitiveness. It is disorganized and shows various degrees of entropy. Entropy is defined as a degree of disorder or randomness within the system.

Figure 2:
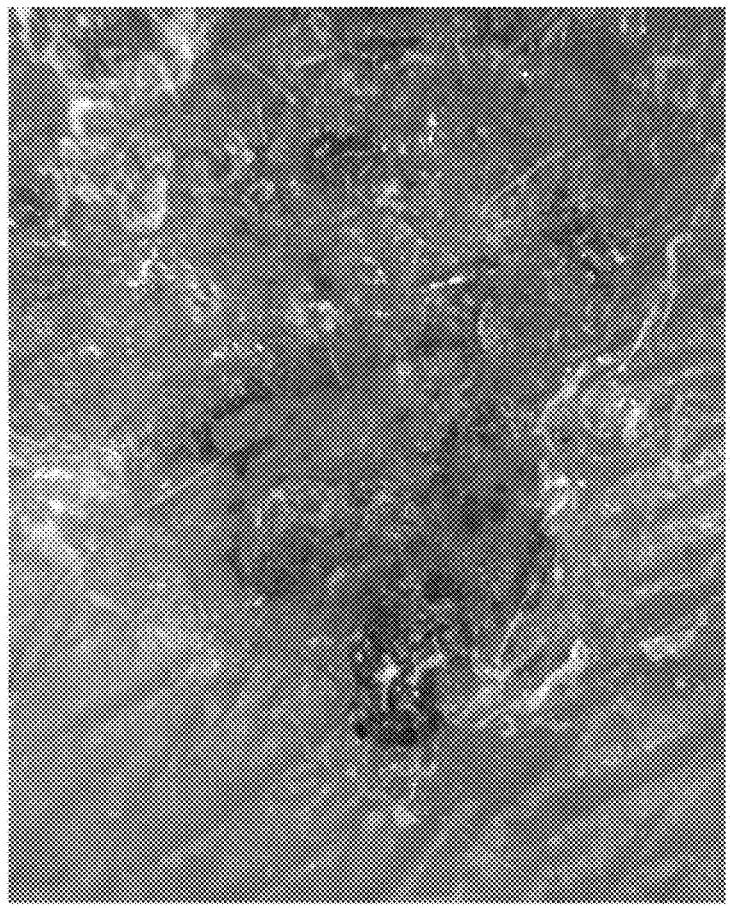
FIG. 2 is a representative image of skin exhibiting a skin disease, according to one embodiment of the present invention.
Figure 3:
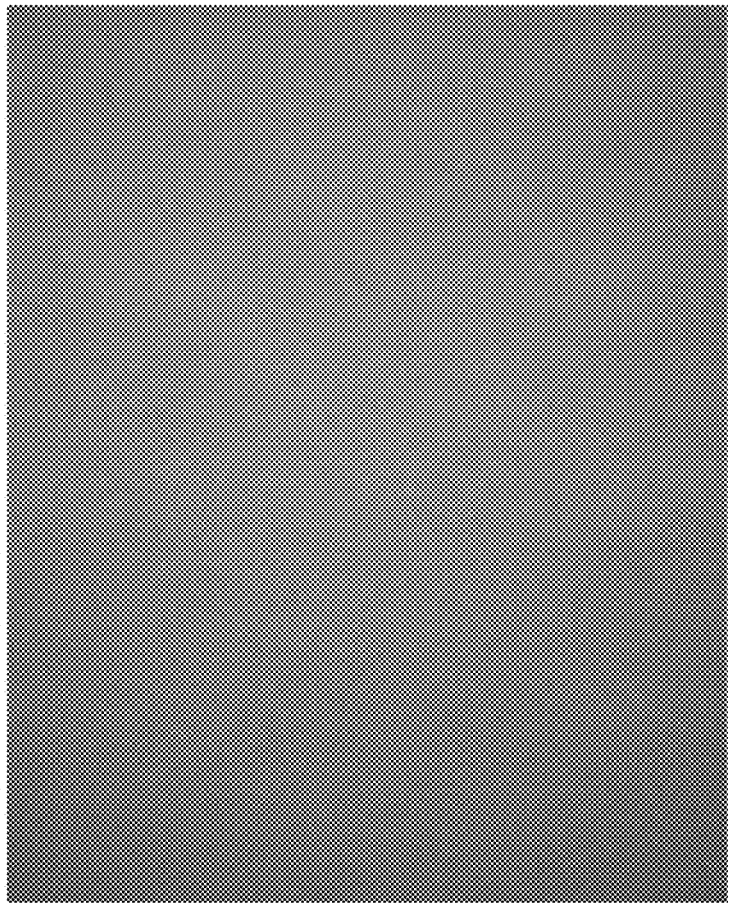
FIG. 3 is a simplified model representation of minimum randomness, according to one embodiment of the present invention.

With reference to FIGS. 1 and 2, and according to one embodiment of the present invention, representative healthy skin image and diseased skin image is shown. The representative skin segment is described herein. The images were taken using a Visioscope PC 35 camera. The resultant images shown an area of 8.00×6.40 mm with resolution of 5:4 and 1280×1024 pixels. The camera employs the parallel polarized light source that helps indicate clinically visible and non-clinically visible redness and scaliness. With specific reference to FIG. 1, an image of a healthy skin is shown. The healthy skin presents a very structured and repetitive form. The color of the skin is ordered and uniform. The skin creases are linear and found in repeated pattern. The topology of the skin is very structured and gives a very flat like, 2-dimensional appearance. The hair follicles are not visible but are very structured in location and form a honey comb shape. With respect to FIG. 2, an image of a skin afflicted with a skin disease is shown. The diseased skin is exhibiting a form or entropy, or randomness, that is not seen on healthy skin. The pattern of skin creases is not uniform, and not repetitive. Furthermore, the diseased skin is exhibiting nonuniform color, with noted reddening in various locations. The scaliness provides additional randomness as it is not uniform throughout the image. The fair follicles are highly irregular in location and length. Finally, the general topology of the diseased skin is very irregular with high degree of variance. A baseline with minimum randomness can be represented by a blank white paper (FIG. 3).

Figure 4:
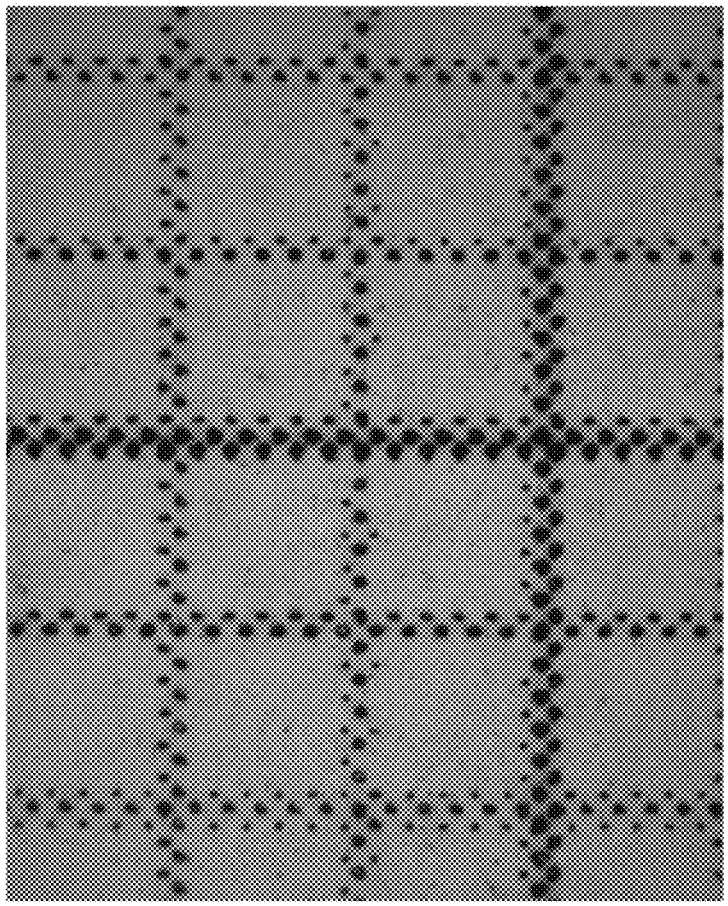
FIG. 4 is a simplified model representation of the order and structure of healthy skin, according to one embodiment of the present invention.
Figure 5:
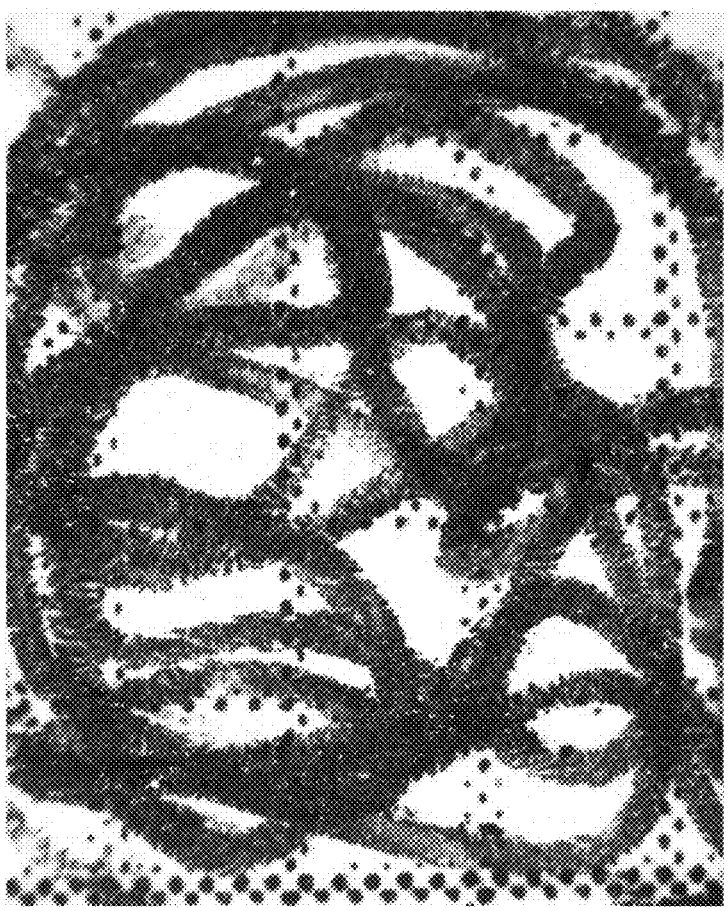
FIG. 5 is a simplified model representation of the level of entropy exhibited by skin with a skin disease, according to one embodiment of the present invention; and, FIG. 6 is a table representing the statistical entropy values of healthy and psoriasis skin of Example 2, according to one embodiment of the present invention.

With reference to FIGS. 4 and 5, and according to one embodiment of the present invention, a simplified model representation of the entropy of diseased skin when compared to healthy skin. The entropy, or level of randomness within the image is representative by the amount of variation within the image. With specific reference to FIG. 4, the simplified model representation of the healthy skin is shown. The image has very regular pattern that is repeating in a very predictable manner. Other patterns may exist, thickly dotted squares, but are not readily identifiable as the pattern is outside of the image frame. With specific reference to FIG. 5, a simplified model representation of a diseased skin is shown. The healthy skin pattern can be detected in background but is overlaid with the expression of the disease that afflicts the diseased skin. The inflammation, scaliness, dryness of skin, irregular hair follicles, and raised skin topology forms the think irregular patterning. The amount of entropy can be assessed as compared to healthy skin to provide a quantitative analysis of the diseased skin.

The level of entropy as described herein provides an additional element, it is able to quantitatively describe the severity of the skin disease. A severe skin disease will have increased entropy as compared to mild to moderate severity. The entropy will provide the physicians the ability to quantify the disease in a numerical scale that is highly reproducible. The quantification will provide new insight on the skin disease and will allow physicians the ability to provide correct treatments and to track the disease progression of patients.

Algorithm

A quantitative method of image analysis has been developed, wherein the image of the skin is segmented and assessed based on regular patterns. One of the most reliable techniques of image analysis is image segmentation. The method works by analyzing and splitting similar characteristics of a simple image. For the quantitative skin assessment, entropy is assessed through an algorithm. The algorithm measures the randomness of an image, and in this case, the randomness of the skin. The algorithm applied:

$$\text{Maximum Entropy: TE}(s) = \max_{s \in G_m} \text{TE}(s)$$

The algorithm provides a method to calculate the quantitative randomness, or entropy, of the skin, which directly correlates to the severity of the skin disease. The higher the entropy, the more severe the skin disease. Skin exhibiting no disease expression will have a lower entropy. The method is quantitative as it can provide a numerical determination of the skin disease, from healthy skin to severe lesions. The calculated Entropy of each Figure was 2.6 (FIG. 1), 3.42 (FIG. 2), 1.81 (FIG. 3), 2.5 (FIG. 4), and 4.7 (FIG. 5). The calculated Entropy corresponds to the degree of randomness, with a higher value equating to a higher degree of observable randomness.

The algorithm produces repeatable results with no physician input that could cause deviation.

Method of Analysis

Skin diseases according to the invention result in physical damage to the skin, which corresponds to a visual assessment of the skin and the severity of the skin disease. According to one embodiment of the present invention, the invention provides a method for determining and quantifying the severity of skin diseases, said method comprising the following steps:
   a. Obtaining at least one skin image of the patient's healthy, non-affected skin;
   b. Obtaining at least one skin image of the patient's disease affected skin;
   c. Determining the level of entropy of the healthy skin by assessment of variation and randomness of the skin image;
   d. Determining the level of entropy of the disease affected skin by assessment of the variation and randomness of the skin image;
   e. Performing a calculation on the entropy of the healthy using the maximum entropy algorithm;
   f. Performing a calculation on the entropy of the disease affected skin using the maximum entropy algorithm; and,
   g. Comparing the calculated entropy between healthy skin and diseased skin and providing a quantitative value for the severity of the diseased skin.

Example 1

The empirical data was obtained through selection of psoriatic skin images from the dermatology clinic database of the deidentified dermatoscopic images. Each image was obtained from patients with clinically confirmed psoriasis. A total of eleven pairs of images were selected. The sample population of selected patients were aged 19 to 73 years old.

The average, standard deviation, and standard error were calculated, as described in Table 1. The data was also cross referenced with the entropy values of blank paper (FIG. 3), gridded paper (FIG. 4), and chaotic pattern (FIG. 5).

The difference among affected and non-affected by the psoriasis skin was assessed through the usage of Mann-Whitney U method. Mann-Whitney U Test was performed on two data sets for normal skin and skin affected by psoriasis. The U-value was determined to be 12. The critical value of U at p<0.5 is 30. Therefore, the current result is significant at the parameter p<0.05. The z-score is determined to be −3.15192. The p-value is 0.00164. The result is significant at the parameter p<0.05. Both results were identified as statistically significant.

Figure 6:
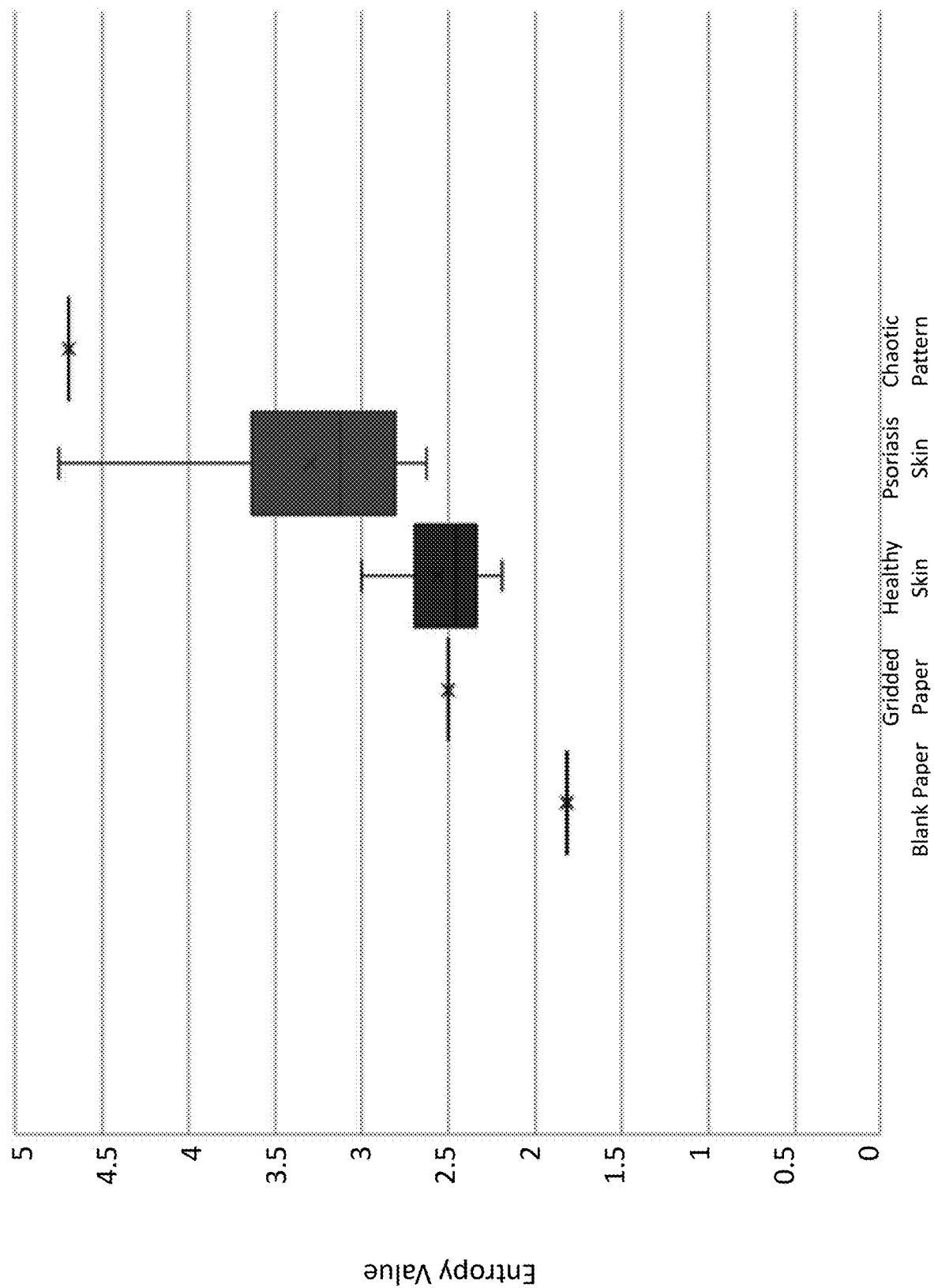

With reference to FIG. 6, and according to one embodiment of the present invention, the statistical representation of entropy values based on different conditions of example 2 is shown. The selected 11 pairs of images from the dermatology clinic database were used to calculate the maximum entropy values of non-affected and psoriasis affected skin. The entropy values of blank paper (FIG. 3), gridded pattern (FIG. 4), and chaotic pattern were used as base lines for the levels of entropy. The calculated entropy level of healthy skin corresponded with the gridded paper control, as healthy skin presents a very structured and repetitive form, similar to that of a gridded paper. The entropy of psoriasis affected skin showed a wide range of entropy, buy was consistently higher than that of healthy skin. The level of entropy of psoriasis skin was dependent on the disease progression and the degree of change to the skin.

The quantitative analysis of the patients was determined to be non-invasive, quick, and very easy to determine and quantify various skin changes and disease progression.

Although certain embodiments have been illustrated and described herein, it will be appreciated by a worker skilled in the relevant art that a wide variety of alternate and/or equivalent embodiments or implementations calculated to achieve the same purpose may be substituted for the embodiments shown and described without departing from the scope of the present invention. A worker skilled in the relevant art will appreciate that the embodiments may be implemented in a very wide variety of applications. The elements described herein is intended to cover any adaptations or variations of the embodiments.

The invention claimed is:

1. A method of quantifying severity of skin disease by determining entropy, comprising:
   identifying a patient with potential skin disease and areas of skin having a non-diseased appearance;
   using a camera to obtain at least one skin image of the patient's healthy, non-affected skin the image comprising individual pixels;
   using a camera to obtain at least one skin image of the patient's disease-affected skin the image comprising individual pixels;

TABLE 1

Sampling data results of entropy values (Overall).

|  | Entropy values |  |  |  |  |  |  |  |  |  |  | Average | SD | SE |
|---|---|---|---|---|---|---|---|---|---|---|---|---|---|---|
| Blank paper | 1.81 | | | | | | | | | | | | | |
| Gridded paper | 2.5 | | | | | | | | | | | | | |
| Healthy skin | 2.6 | 2.45 | 2.69 | 3.28 | 2.41 | 2.49 | 2.19 | 2.27 | 3 | 2.34 | 2.39 | 2.56 | 0.33 | 0.1 |
| Psoriasis skin | 3.42 | 3.53 | 3.12 | 4.76 | 2.91 | 3.13 | 3.64 | 2.63 | 3.7 | 2.64 | 2.81 | 3.30 | 0.62 | 0.19 |
| Chaotic pattern | 4.7 | | | | | | | | | | | | | |

SD—Standard Deviation, SE—Standard error.

The entropy values for normal skin in Example 2 shown normal distribution with mean μ=2.56 ±0.10 and standard deviation σ=0.33. The 95% confidence interval is [2.36, 2.75]. The entropy values for skin affected by lesions show normal distribution with mean μ=3.30 ±0.19 and standard deviation σ=0.62. The 95% confidence interval [2.93, 3.66].

determining a level of entropy of the healthy skin by assessment of variation and randomness of pixel information of the at least one skin image;
   determining a level of entropy of the disease-affected skin by assessment of the variation and randomness of pixel information of the at least one skin image;

performing a calculation of the entropy of the healthy skin by using a maximum entropy algorithm on the at least one skin image of the patient's healthy, non-affected skin;

performing a calculation of the entropy of the disease-affected skin by using the maximum entropy algorithm on the at least one skin image of the patient's disease-affected skin; and comparing the calculated entropy between healthy skin and diseased skin and providing a quantitative value for severity of the diseased skin.

2. The method of quantifying severity of skin disease by determining entropy of claim 1 wherein skin disease comprises psoriasis.

3. The method of quantifying severity of skin disease by determining entropy of claim 1 wherein said method is non-invasive.

4. The method of quantifying severity of skin disease by determining entropy of claim 1 wherein correlation between entropy of the diseased skin and the severity of skin disease is direct.

5. The method of quantifying severity of skin disease by determining entropy of claim 1 wherein quantification of entropy uses a maximum entropy algorithm.

* * * * *